United States Patent [19]

Mancini et al.

[11] 3,957,362

[45] May 18, 1976

[54] HYDROGELS AND ARTICLES MADE THEREFROM

[75] Inventors: William L. Mancini, Framingham; Donald R. Korb, Boston; Miguel F. Refojo, Lexington, all of Mass.

[73] Assignee: Corneal Sciences, Inc., Boston, Mass.

[22] Filed: Mar. 18, 1974

[21] Appl. No.: 451,906

Related U.S. Application Data

[63] Continuation-in-part of Ser. No. 294,019, Oct. 2, 1972, abandoned.

[52] U.S. Cl. ............................... 351/160; 128/130; 264/1; 260/2.5 R; 260/29.6 R; 424/81; 526/230; 526/320
[51] Int. Cl.² ................... C08F 220/14; G02C 7/04
[58] Field of Search ........... 351/160; 264/1; 424/81; 128/130; 260/86.1 E, 2.5 R, 80.72, 29.6 R

[56] References Cited
UNITED STATES PATENTS

| | | | |
|---|---|---|---|
| 2,976,576 | 3/1961 | Wichterle et al. | 264/1 |
| 3,220,960 | 11/1965 | Wichterle | 260/2.5 |

OTHER PUBLICATIONS

Yasuda et al., Die Makromolekulare Chemie 118 (1968), pp. 19 and 22–24.

Yasuda et al., J. Pol. Sci., Part A-2, Vol. 9, (1971), pp. 1117 and 1122–1124.

*Primary Examiner*—Harry Wong, Jr.
*Attorney, Agent, or Firm*—Robert L. Goldberg

[57] ABSTRACT

This invention relates to copolymers and hydrogels formed by copolymerization of a hydrophilic monomer from the group of dihydroxyalkyl acrylates and methacrylates and a substantially water insoluble monomer from the group of alkyl acrylates and methacrylates. The preferred copolymer of the invention is formed from methyl methacrylate and glyceryl methacrylate (2,3-dihydroxypropyl methacrylate). The hydrogels of the invention have unique physical and physiological properties which are particularly useful for the formation of contact lenses, particularly contact lenses having a relatively thin cross-section, though they may also be used for other purposes such as drug and pesticides delivery devices, dialysis, ultrafiltratiaon and reverse osmosis membranes, implants in surgery and dentistry and the like.

32 Claims, No Drawings

HYDROGELS AND ARTICLES MADE THEREFROM

This application is a continuation-in-part of my co-pending U.S. application Ser. No. 294,019 filed Oct. 2, 1972, and now abandoned.

BACKGROUND OF THE INVENTION

1. Introduction

This invention relates to copolymers of alkyl acrylates or methacrylates and dihydroxyalkyl acrylates or methacrylates which copolymers are particularly useful for the formation of contact lenses.

2. Description of the Prior Art

As is known in the art, the conventional contact lens is made from methyl methacrylate. Lenses made from this material, known as "hard lenses," have had only limited success because many people cannot adapt to the presence of the lens in the eye and/or the lens compromises the physiological processes required for corneal metabolism. For many people, minor irritations are caused by small particles and dust which become lodged under the lens and rub against the cornea. Moreover, it has been found that after wearing hard contact lenses for extended periods of time — e.g., from 1 to 5 years, with varying degrees of success, many people develop discomfort and are forced to discontinue wearing the lenses.

In view of the above, there has been considerable research in an effort to develop new contact lens materials which would overcome some of the problems of the methyl methacrylate lens described above. A class of such materials is described in U.S. Pat. Nos. 2,976,576 and 3,220,960 incorporated herein by reference. The materials described in these patents are hydrogels of a sparingly cross-linked hydrophilic polymer and a substantial quantity of an aqueous liquid — e.g. water. The hydropilic polymer is actually a copolymer of a major amount of a polymerizable monoester of an olefinic acid selected from the group of acrylic and methacrylic acids having a single olefinic double bond and a minor amount of a polymerizable diester of one of said acids, the diester having at least two olefinic double bonds. The copolymer is formed by copolymerization in a solvent medium.

Within the class of materials disclosed in these patents is a slightly cross-linked polymer comprising a predominant amount of 2-hydroxyethyl methacrylate. This polymer, known in the art as "Hema", has been primarily used for contact lenses. Hema has the significant characteristic of forming hydrophilic polymers capable of hydration with water — e.g., typically about 40% by weight. (However, the percent may vary from approximately 35 percentage to 65 percent by weight). This high water content renders the contact lens made from the material quite flexible and soft, with the result that such a lens is able to mold itself to the curvatures of the eye more readily. This is in contrast to the conventional hard lens, which maintains a rigid manufactured configuration and does not conform to the eye's curvature.

The most significant advantage of the Hema hydrogel soft lens is that with proper design, it can be worn with almost immediate and continuing comfort as the cornea appears to suffer less discomfort than with the conventional hard lens at least initially. A second advantage of the Hema hydrogel soft lens is that relative to the hard lens, the problem of dust and foreign bodies becoming lodged beneath the lens and rubbing against the cornea is reduced. Still another advantage of the Hema hydrogel soft lens, as compared with the conventional hard lens, is improved peripheral vision resulting from the use of larger lens diameter.

Despite the advantages of the Hema hydrogel soft lens, there are still certain problems that have prevented, at least to date, the universal acceptance and use of such a lens. One such problem involves the lack of clarity of central vision. For many persons, the Hema hydrogel soft lens does not provide adequate and steady vision because the nature of the material results in a constantly changing optical surface during eye movement and blinking, possibly due to the lens being too soft or non-rigid. A second problem concerns the correction of astigmatism. Conventional hard contact lenses are usually able to correct corneal astigmatism by providing a new surface on the cornea. Because of the extreme flexibility of the Hema hydrogel soft contact lens, the lens will conform to the shape of the eye and therefore, in most cases, will not provide the new surface necessary to correct astigmatism. Other physiological problems have been found with existing Hema hydrogel soft contact lenses. These include corneal irritation and folds in the membranes of the eye. The exact causes or significance of these phenomena are not known, nor are there reported solutions. However, it has been reported that lacrimal interchange with Hema lenses is minimal as compared to conventional lenses, possibly because of the manner in which the lens conforms to the contour of the eye thereby preventing the flow of lacrimal fluid beneath the edge of the lens. The reduction in fresh lacrimal fluid is not desirable as it substantially reduces the contact of the eye with oxygen and relief from accumulation of catabolic products. Finally, the Hema hydrogel soft lens has been reported to have a tendency to tear easily, requiring replacement each time this occurs.

As will be discussed in greater detail below, there is provided herein a new hydrogel material suitable for the formation of contact lenses comprising a copolymer of hydrophilic monomers selected from the group of dihydroxyalkyl acrylate and methacrylate and a substantially water insoluble monomer selected from the group of an alkyl acrylate and a methacrylate, said hydrogel being formed by a bulk, free radical polymerization reaction. The preferred reactants are glyceryl methacrylate, and methyl methacrylate in certain specific proportions. Similar copolymers formed from the two preferred monomers are known in the art and described by H. Yasuada, C. E. Lamazo, and L. D. Ikenberry, Makromol. Chem. 118, 1935 (1968) and H. Yasuada, C. E. Lamaza and A. Peterline, J. Polym Sc. Part A-2, 996, 1117–1131 (1971).

The copolymers described in the first of the above two publications were polymerized in a 70/30 acetic acid/water solvent system. The solutions were prepared with 5% weight total monomer and 95% solvent, and initiated with approximately 0.5% (based on monomer weight) $K_2S_2O_8$ and 1% $Na_2S_2O_2$. Oxygen in the solutions was purged by bubbling nitrogen through the solution. After 8 to 10 days at room temperature, precipitation of the polymer was effected in water. Six copolymers were made in this series having ratios of methyl methacrylate and glyceryl methacrylate of from 95:5 to 70:30 (monomer mole ratio).

The procedure followed in the second of the above-noted publications was similar to the first except that the polymerization reaction was carried out in a non-aqueous solvent with 2,2' azobis (2 methyl propionitrile) as the initiator. For reasons to be discussed more fully below, the copolymers of these two references differ from those described herein as a result of the polymerization method used and the ratio of components, the compolymers of the references not having properties suitable for the purposes of this invention, especially with respect to the formation of contact lenses.

SUMMARY OF THE INVENTION

As noted above, there is provided herein a copolymer formed from a hydrophilic monomer from the group of dihydroxyalkyl acrylates and methacrylates and a substantially water insoluble monomer selected from the group of alkyl acrylates and methacrylates (hereinafter referred to as the "dihydroxyalkyl acrylate" and "acrylate", respectively). The copolymer is preferably formed by free radical, bulk polymerization in the substantial absence of solvent or diluent as this procedure provides copolymers having properties substantially superior to polymers formed by other methods, especially for use as contact lenses. The dihydroxyalkyl acrylate is preferably used in major amount and the alkyl acrylate is preferably used in minor amount.

The copolymers formed herein have properties similar to those of the Hema materials described above and consequently, are also suitable for the formation of contact lenses as well as other items that must be assimilated with living tissue such as surgical implants. However, contact lenses formed from the copolymers of this invention do not have many of the disadvantages of the lenses formed from the Hema material. In this respect, though the copolymers of the invention are soft and supple as required by a soft contact lens, they are also stronger and somewhat stiffer than the Hema materials. As a result, they provide adequate and steady vision because a constantly changing optical surface does not occur with eye movement and blinking such as to interfere with vision. Also, because the copolymers of the invention are stiffer than the Hema materials, the lenses formed from the copolymers of this invention may be designed with peripheral curvatures which maximize fluid flow thus providing fresh lacrimal fluid to those areas covered by the lens which fluid provides oxygen and also moves catabolic products and other dust or dirt particles which might accumulate underneath the lens. Moreover, and perhaps more importantly, the added stiffness permits fabrication of lenses of thinner cross-section than lenses formed from the Hema materials. This thinner cross-section results in substantial permeability whereby the lacrimal fluid is capable of flowing through the lens as well as around its edges. Consequently, eye irritation typically experienced with the Hema lenses is avoided. Other advantages of the contact lenses formed from the copolymers of this invention include and improved ability to clean with water and a toughness which prevents tearing.

DESCRIPTION OF THE PREFERRED EMBODIMENTS

The hydrophilic dihydroxyalkyl acrylate which is one component of the copolymer described herein conforms to the following general formula:

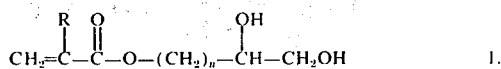

I.

where R is hydrogen or a methyl group and $n$ is an integer having a value of from 0 to 4, inclusive.

The dihydroxyalkyl acrylate can be formed by hydrolysis following the procedures set forth in British Patent No. 852,384 incorporated herein by reference. In this patent, a particular dioxolanoalkyl acrylate or methacrylate is hydrolyzed with a dilute aqueous solution of a strong mineral acid for an extended period of time at about room temperature as illustrated below.

Example 1

Fifty grams of isopropylideneglyceryl methacrylate, 150 ml of water, 0.3 g. of concentrated sulfuric acid, and 0.02 of hydroquinone were stirred for 16 hours at 25°–30°C. A clear colorless solution was obtained. The sulfuric acid was neutralized by the addition of a small amount of solid barium hydroxide. The precipitate of barium sulfate was removed by filtration and washed on the filter with a little water. The filtrate and washings were combined to give 212 ml of a clear, colorless solution, calculated to consist of an approximately 20% solution of 2,3—dihydroxypropyl methacrylate in dilute aqueous acetone (12/1). The product is isolated by saturation with sodium chloride and extracted with benzene or ether. After stripping off the solvent at reduced pressure, 2,3—dihydroxypropyl methacrylate is obtained as a slightly viscous oil.

The preferred comonomer for preparation of the hydrogel copolymers of this invention is glyceryl methacrylate (2,3—dihydroxypropyl methacrylate). This material may be made by the process set forth in the above reference British patent, but is preferably made in accordance with the process described by M. F. Refojo in Journal of Applied Polymer Science, Volume 9, Pages 3161 to 3170 (1965). This process involves the hydrolysis of glycidyl methacrylate and solvent extraction from the reaction mixture subsequent to the hydrolysis reaction as illustrated below.

Example 2

One hundred grams of commercial glycidyl methacrylate (American Aniline and Extract Company, Inc.-GMA), 150 ml distilled water and 0.25 ml of concentrated sulfuric acid were stirred for 6 days. During the experiment, the reaction flask was kept in a water bath at 24°–29°C. No additional inhibiting agent was added to the reaction mixture other than the amount present in the commercial glycidyl methacrylate.

Glycidyl methacrylate is immiscible with water, but as the reaction proceeds, solubility is increased until a clear solution is obtained. As the reaction proceeds, glyceryl methacrylate is formed which co-dissolves the unreacted glycidyl methacrylate.

The reaction mixture was neutralized with 10% sodium hydroxide and then extracted with five 100 ml portions of ether. The ether extract was washed with three 20 ml portions of distilled water, then this aqueous solution was washed again with 50 ml of ether. The combined ether extracts were dried with anhydrous sodium sulfate. The ether was then evaporated in a rotating evaporator with the rotating flask kept in a cool water bath. The residue from the ether extract, 18.8 g, was mainly glycidyl methacrylate which could be used to prepare more glyceryl methacrylate.

The aqueous extract from the ether solution was saturated with sodium chloride. The glyceryl methacrylate separated out as an oily layer above the saturated saline solution. The oily material was dissolved in methylene chloride. The organic solution was dried with anhydrous sodium sulfate and evaporated, without heating, by using the same procedure described above for the concentration of the ether extract. The residue from the evaporation (11.6 g) was a viscous, clear liquid, mainly glyceryl methacrylate.

The aqueous reaction medium, previously extracted with ether, upon saturation with sodium chloride, separated into two layers. The organic layer was taken up with methylene chloride and the solution, after being dried with anhydrous sodium sulfate, was evaporated in the rotating evaporator by using a cool water bath under the rotating flask. The yield was 71.6 g. of glyceryl methacrylate. This reaction product also contained between about 1.8% and 2.2% by weight of unreacted glycidyl methacrylate which was not removed in the extraction step. Minor amounts of other impurities, such as methacrylic acid, glyceryl methacrylate diester and/or glyceryl methacrylate triester, may also have been present.

It should be understood that other dihydroxyalkyl acrylates can be made from the corresponding epoxy alkyl esters by the process described in the above example 2.

The other comonomer used with the dihydroxyalkyl acrylate is a substantially water insoluble alkyl acrylate or methacrylate corresponding to the following general formula:

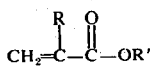
2.

where R is hydrogen or methyl and R' is alkyl having from 1 to 6 carbon atoms. Materials conforming to the above general structure are commercially available and require no further description. Examples of materials conforming to this formula include, for purposes of illustration, methyl acrylate, methyl methacrylate, ethyl acrylate, ethyl methacrylate, propyl methacrylate, butyl acrylate and butyl methacrylate. Methyl methacrylate is a preferred material.

The ratio of the dihydroxyalkyl acrylate to the alkyl acrylate can vary within rather broad limits. Thus, the molar ratio of the dihydroxyalkyl acrylate to the alkyl acrylate can range between 1:3 and 20:1. However, it is preferred that the dihydroxyalkyl acrylate be at least equal to or in excess of the alkyl acrylate and in this respect, a preferred molar ratio varies between about 1:1 and 10:1 and most preferably between 1.2:1.0 and 2:1. For use as a contact lens, it is most preferable that the aforesaid molar ratio be about 1.5:1.0.

The polymerization procedure and the catalyst materials useful therefore are in accord with prior art procedures applied to monomers through preferably bulk polymerization procedures are used substantially in the absence of solvent, with the monomers described herein. The copolymers formed by such bulk polymerization procedures have properties differing from similar prior art copolymers made using solution polymerization procedures. Thus, according to the preferred method, the monomers are mixed in the absence of solvent, maintained at an elevated temperature for a prolonged period of time and the resulting polymer is recovered. Typically, the temperature of the polymerization reaction varies between 20° and 60°C, preferably varies between 35° and 42°C and most preferably is maintained at about 40°C. The catalyst concentration may vary within rather broad limits dependent upon the particular catalyst used but generally varies between 0.001 and 0.2 weight percent of the hydroxyalkylacrylate and preferably between 0.01 and 0.04 weight percent. A preferred catalyst is isopropyl percarbonate in an amount of about 0.02 weight percent.

It appears that at least a major part of whatever crosslinking of the dihydroxyalkyl acrylate/alkyl acrylate polymer chains takes place because of the presence of unreacted epoxy alkyl ester remaining in the dihydroxyalkyl acrylate reaction product. Normally an appreciable amount of unreacted epoxy alkyl ester will remain in the reaction mixture even after repeated solvent extraction steps. This is apparently due to the dihydroxyalkyl acrylate acting as a cosolvent for the ester in the aqueous phase. However, if the amount of unreacted ester present in the dihydroxyalkyl acrylate product is different from the amount necessary in order to get the desired degree of crosslinking, it can be adjusted by addition of epoxy alkyl ester to increase crosslinking or by reducing the amount of ester in the product in order to decrease crosslinking. The amount of ester can be reduced, for example, by further solvent extraction steps, as is well known in the art.

The amount of epoxy alkyl ester which should be present in the reaction product depends on the degree of crosslinking desired in the final hydrogel product. Generally, the higher the amount of epoxy alkyl ester, the higher the degree of crosslinking which will be obtained and the lower the amount of ester, the lower the amount of crosslinking. Generally, it is preferred to have from about 1 to 3% by weight epoxy alkyl ester in the dihydroxyalkyl acrylate which is reacted with the alkyl acrylate. In the preferred glyceryl methacrylate/methyl methacrylate system, for example, reaction using glyceryl methacrylate containing about 1% by weight glycidyl methacrylate will generally yield a copolymer which will be hydrated about 53% indicating relatively low degree of crosslinking, whereas the use of glyceryl methacrylate containing about 3% glycidyl methacrylate will generally yield a copolymer which will be hydrated about 32%, indicating a relatively high degree of crosslinking. A preferred range for the epoxy alkyl ester is from about 1.8% to 2.2% by weight, which in the preferred system gives glyceryl methacrylate/methyl methacrylate copolymers having about 39–43% hydration. While not wishing to be bound by theory, it is possible that the crosslinking reaction proceeds by the formation of a free radical on the carbon atom containing the tertiary hydrogen that is alpha to the epoxide oxygen atoms. The thus obtained radical for glycidyl methacrylate is shown below:

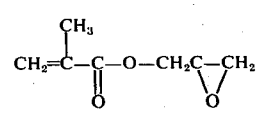

Small amounts of other impurities, e.g., methacrylic acid from possible acid hydrolysis of the glycidyl methacrylate and/or the dimer or trimer of glyceryl methacrylate, if present will react with the glyceryl methacrylate/methyl methacrylate copolymer and may aid to a small degree the crosslinking thereof. However, it is clear that the essential crosslinking agent is the epoxy alkyl ester, and that compound is effectively used to control the amount of crosslinking obtained. Other polymerizable difunctional compounds having only one olefinic double bond, the other functional group being non-olefinic, may also be used as the crosslinking agent. Other suitable crosslinking agents are known to those skilled in the art.

Example 3

A mixture comprising 56.8 g. of 2,3—dihydroxypropyl methaacrylate (made in accordance with Example 2 above) and 23.7 g. of methyl methacrylate (Rohm and Haas Company, Inc.-mole ratio of 1.5:1.0) was stirred thoroughly. Approximately 3 g. of sodium sulfate were added to the mixture with stirring. This acted as a dessicant to remove all traces of water. The mixture was then filtered to remove the sodium sulfate and 15.5 mg (0.02 weight percent of the 2,3—dihydroxypropyl methacrylate) of isopropyl percarbonate were added. The mixture so formed was stirred thoroughly and placed in a large tube.

The tube containing the mixture was put in a low temperature bath of dry ice in methylene chloride so that the temperature of the mixture in the tube was maintained between -20° and -30°C. The tube was purged with nitrogen three times, sealed under vacuum and placed in a constant temperature bath maintained between 35° and 40°C to cause the polymerization reaction to occur. Temperature was maintained for about 4 hours though after about 90 to 95 minutes, the mixture had solidified indicating the reaction had taken place. This point in the reaction, where solidification occurs, will be hereinafter referred to as the "polymerization time". Thereafter, the tube was placed in an oven maintained at 75°C for about 16 hours (overnight). The temperature of the oven was then raised to 90°C and held at this temperature for 1 hour. Thereafter, the tube was allowed to cool.

The polymer formed by the above procedure could be removed from the tube in the form of a solid rod. This material, when cut into thin discs or shaped into lenses, and placed in water, would become hydrated and develop a soft, rubbery consistency.

Examples 4 – 8

The procedure of example 3 was repeated several times with variation in the ratio of the 2,3—dihydroxypropyl methacrylate (GMA) to the methyl methacrylate (MMA). The catalyst concentration was maintained at 0.02 weight percent of the 2,3—dihydroxypropyl methacrylate and the polymerization temperature was carefully maintained at 40°C. Following the reaction procedure, the polymer was evaluated in terms of percent hydration, percent linear swelling, durometer hardness and appearance in the hydrated state. The ratios used and results obtained are set forth in the following table:

| Ex. No. | Ratio GMA:MMA | Hydration percent | Lin. Sw.[1] | D.R.[2] | Appearance[3] |
|---|---|---|---|---|---|
| 4 | 1:1 | 27–29 | 12–14 | — | VM |
| 5 | 1.25:1 | 33–35 | 14–16 | 53–56 | VM |
| 6 | 1.5:1 | 39–42 | 17–19 | 46–49 | SM |
| 7 | 2:1 | 43–45 | 20–22 | 39–43 | SC |
| 8 | 3:1 | 50–52 | 25–27 | — | C |

[1]Linear swelling (percent)
[2]Durometer reading-Shore Durometer Type A-2(0–60) ASTM D 676.
[3]Appearance determined by viewing a round button, 3 mm thick having a 12 mm diameter through the edge or cross-section of the button.

The symbols used and their meaning are as follows:
VM—very milky, SM—slightly milky, SC—slightly clear, C—clear.

In the above examples 6 is the preferred material for fabrication of contact lenses even though slightly milky when viewed through the cross-section of the button, possibly due to a lack of homogenity which could account for the improved stiffness of the hydrated copolymer. The preference for example 6 is based upon the physical properties of the polymer (hardness and rigidity) which are optimum for the fabrication of lenses. In fact, it has been discovered that for contact lens fabrication in general, a guide to optimum properties in accordance with the invention is the slightly milky appearance of the polymer when viewed through the edge or cross-section of the button having the aforesaid dimensions. With regard to optical clarity of a lens fabricated from the preferred polymers, in the thin sections used (0.05 to 0.15 mm) the appearance of the lens is one of virtually absolute optical clarity.

Examples 9 – 14

The procedure of examples 3 was repeated several times but the concentration of catalyst was increased. The temperatures of polymerization was maintained constant at 40°C. The result of increased concentration of catalyst was an expected decreased reaction time (the time in which a solid forms in the tube containing the monomers). The results are set forth in the following table:

| Ex. No. | Catalyst percent | P.T.[1] | Hydration percent | Lin.Sw.[2] | D.R.[3] | Appear.[4] |
|---|---|---|---|---|---|---|
| 9 | 0.02 | 93 | 39–42 | 17–19 | 46–49 | SM |
| 10 | 0.03 | 60 | 41 | 20 | 46 | SM |
| 11 | 0.04 | 45 | 41 | 18 | 47 | SC |
| 12 | 0.05 | 34 | 40 | 20 | 47 | SC |
| 13 | 0.06 | 28 | 41 | 20 | 47 | C |

-continued

| Ex. No. | Catalyst percent | P.T.[1] | Hydration percent | Lin.Sw.[2] | D.R.[3] | Appear.[4] |
|---|---|---|---|---|---|---|
| 14 | 0.08 | 18 | 42 | 20 | 46 | C |

[1]Polymerization time-minutes
[2]Linear Swelling-percent
[3]Durometer reading
[4]appearance-see footnote (3) following table for examples 4–8.

Example 9 represents a polymer preferred for fabrication of contact lenses, again exhibiting a slightly milky appearance viewed through the cross-section of a standard sized button.

Examples 15 – 17

The procedure of Example 3 was repeated several times, except that temperature was varied, all other conditions being maintained constant, with results as follows:

| Ex. No. | Temp °C. | P.T.[1] | Hydration percent | Lin.S.[2] | D.R.[3] | App.[4] |
|---|---|---|---|---|---|---|
| 15 | 40 | 93 | 39–42 | 17–19 | 46–49 | SM |
| 16 | 43 | 42 | 41 | 20 | 47 | SC |
| 17 | 45 | 39 | 42 | 20 | 46 | SC |

[1]Polymerization time-minutes
[2]Linear Swelling-percent
[3]Durometer reading
[4]Appearance-see footnote(3) following table for examples 4–8.

The copolymer of Example 15 is preferred for contact lens use. From a review of the aforesaid Examples 4–17, it can be seen that for contact lens fabrication, it is preferred that there be a ratio of the 2,3—dihydroxypropyl methacrylate to methyl methacrylate of about 1.5:1, an isopropyl percarbonate concentration of about 0.02 weight percent based upon the 2,3—dihydroxypropyl methacrylate and a reaction temperature of about 40°C, preferably followed by curing.

Example 18

The procedure of Example 13 may be repeated substituting ethyl methacrylate for methyl acrylate with similar results expected.

Example 19

The procedure of Example 3 may be repeated substituting methyl acrylate for methyl methacrylate with similar results expected.

Example 20

The procedure of Example 3 may be repeated substituting 2,3—dihydroxypropyl acrylate for 2,3—dihydroxypropyl methacrylate with similar results expected.

Example 21

Two hundred grams (1.406 mol) of glycidyl methacrylate, 300 ml of water and 0.5 ml of concentrated sulfuric acid was stirred for 5 days at 24°–29°C. The resultant clear solution had a pH of 2.0 and was made neutral to pH 7.0 with 10% sodium hydroxide solution. The solution was then extracted with six 100 ml portions of ether. The aqueous layer was stirred and saturated with sodium chloride, resulting in a two phase mixture which was separated by filtration. The two phase filtrate was then extracted with six 100 ml portions of methylene chloride. The combined extracts were stored in a separatory funnel overnight in a refrigerator to clear. The organic layer was separated and concentrated under reduced pressure to yield 118.7 grams of a clear viscous liquid, mainly glyceryl methacrylate but containing 2.19% by weight unreacted glycidyl methacrylate. A portion of this reaction product (62.6 gm) was mixed with 26.1 gm of methylmethacrylate. This solution was dried by treatment with sodium sulfate and filtration of the resultant mixture. The filtrate was mixed thoroughly with 18.2 mg of isopropyl percarbonate, and put into four large treated test tubes. Nitrogen was bubbled through each tube for 2 minutes, and the tubes were cooled to −30°C, evacuated and filled with nitrogen (three times) and sealed under vacuum. After coating the tips with wax, the tubes were put into a constant temperature bath at 40°C for 5 hours. The tubes were then put into an oven at 75°C overnight. The next morning the temperature was increased to 90° for 1 hour. Afterwards, the tubes were cooled. Test buttons made from this batch exhibited 39.3% hydration and 17.9% swelling. Subjecting the glyceral methacrylate to further solvent extraction until it contained only 1.06% unreacted epoxide resulted in a polymer having 52.8% hydration.

As noted above, the hydrogels of this invention have properties which make them excellent materials for soft contact lens application. Thus, after absorbing water (or physiological saline water or water containing a physiologically active solute such as a bacteriostatic agent) the hydrogels are soft and flexible, but at the same time, they are tough and resist tearing. They are somewhat more rigid than prior art materials used for hydrogel contact lenses and consequently, maintain the contour of the eye to a greater extent than prior art materials and may be fabricated in thinner cross-section, typically from 0.05 to 0.15 mm in thickness. With this thin cross-section, they are substantially more permeable to lacrimal fluid than prior art materials. Moreover, the increased rigidity prevents misshaping by blinking thus preventing an everchanging optical surface resulting in variations and distortions of vision. While of adequate flexibility to conform to the cornea if properly designed, they are sufficiently rigid to maintain their shape thus permitting a flow of lacrimal fluid underneath the lens. This is an advantage as it provides fresh lacrimal fluid and nutrients to those areas covered by the lens and also relieves catabolic products which might accumulate underneath the lens. Moreover, the materials are sufficiently rigid to permit the design and function of peripheral curvature to the lens to maximize this fluid flow.

In addition to the above utility of the copolymers of this invention, the physiochemical properties make them suitable for prolonged contact with living tissue, blood and the mucous membrane such as would be required for surgical implants, blood dialysis devices and the like. In this respect, it is known that blood, for example, is rapidly damaged when in contact with most artificial surfaces. The design of a synthetic surface which is antithrombogenic and nonhemolytic to blood is necessary for any prosthesis end device to be used with blood. The non-ionic hydrogels, such as those of the subject invention, are known to substantially reduce the clotting tendency of blood.

The hydrogels are also selectively permeable to water and thus, they qualify for various applications involving dialysis, ultrafiltration, and reverse osmosis. In this respect, it is particularly advantageous that the permeability of these hydrogels may be adapted for any desired purpose and the size and shape of a diaphragm may be prepared in situ to form an integral part of a hydrophilic article or device. The good chemical stability of the hydrogels also make them suitable for electrolytic purposes.

The method of forming hydrophilic articles according to the invention may be modified in such a manner that the dialytic effectiveness is substantially increased. It is possible to form a system of parallel narrow channels or conduits in the diaphragm which are separated by a comparatively thin layer of the hydrogel. The dialized liquids flow either counter current or in the same direction through adjacent conduits. The system of conduits in a diaphragm may be prepared by placing fibers or sheets made of a subsequently removable substance, in a mold, and then pouring the polymerization mixture into the mold. After polymerization, the fibers or sheets are removed by dissolution in an appropriate agent.

A very suitable material for this purpose is glass fibers which can be removed from the hydrogel article by means of hydrofluoric acid. This acid and the silicofluoric acid formed by the reaction are readily soluble and are washed from the article. Other suitable materials are aliphatic polyesters melting at temperatures below 100°C., which may be melted out, any residue then being removed by means of ethyl acetate.

The arrangement of the channel or conduit system in the diaphragm may be modified for special purposes; e.g. for industrial dialytic proceses or for the construction of an artificial kidney. The mentioned examples are only illustrative, without limiting the scope of the invention.

The copolymers of the subject invention can also be impregnated with a drug. Then when the copolymer, in the form of an article made therefrom such as an intrauterine device is administered to a patient, the drug will gradually be released to the patient. As the drug is rinsed from the surface of the copolymer, it will be replaced with a fresh supply of drug migrating to the surface of the compolymer from its interior.

In a similar manner, the copolymers may be used for controlled release of pesticides. Pesticides released gradually by diffusion from the copolymer, particularly biodegradable pesticides when applied in this manner, will reduce environmental hazards associated with the continued usage of conventional pesticides.

The entire article prepared according to this invention forms a lattice of giant swollen molecules when immersed in water. It is therefore not only permeable to water and to certain aqueous solutions, but also strong, of stable shape and very elastic. It can be boiled in water without being damaged whereby thorough sterilization may be achieved. These properties make an article formed from the copolymer of the invention suitable for purposes in surgery, where a body compatible with living tissue or with a mucuous membrane may be used, e.g.— for making contact lenses as described above, for filling or dividing cavities in tissue, for pessaries, etc.

It is obvious that chemical equivalents of the monomers mentioned in the above application and examples may be used without exceeding the scope of this invention.

We claim:

1. A contact lens of a copolymer formed by the free radical bulk polymerization of a mixture consisting essentially of two acrylic monomers in the substantial absence of water or other diluent, said first monomer being hydrophilic and conforming to the formula:

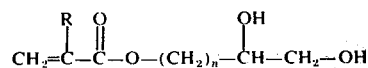

where R is hydrogen or methyl and $n$ is a whole integer having a value of from 0 to 4, and said second monomer being substantially water insoluble and conforming to the formula:

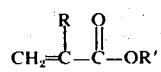

where R is as above described and R' is alkyl having from 1 to 6 carbon atoms, the mole ratio of said first acrylate to said second acrylate varying between 1:1 and 10:1, said copolymer being insoluble in a solvent system comprising 60% by volume acetone and 40% by volume dioxane.

2. The contact lens of claim 1 where the mole ratio of said first acrylate of said copolymer to said second acrylate varies between 1.2:1 and 2:1.

3. The contact lens of claim 1 where the reaction temperature of the copolymerization reaction is about 40°C.

4. The contact lens of claim 1 where the R of each of said acrylates is methyl.

5. The contact lens of claim 1 where R of said first and said second acrylates and R' of said second acrylate are methyl and n is 1.

6. The contact lens of claim 1 where the copolymer is formed under conditions whereby a hydrated round button formed from said copolymer having a thickness of 3 mm and a diameter of 12 mm will appear slightly milky when viewed through its cross-section.

7. A contact lens of a copolymer formed by free radical bulk polymerization of a mixture consisting essentially of 2,3—dihydroxypropyl methacrylate and methyl methacrylate in the substantial absence of water or other diluent, the molar ratio of 2,3—dihydroxypropyl methacrylate to methyl methacrylate ranging between about 1:1 and 10:1 said copolymer being insoluble in a solvent system comprising 60% by volume acetone and 40% by volume dioxane.

8. The contact lens of claim 7 where the mole ratio of 2,3—dihydroxypropyl methacrylate of said copolymer to the methyl methacrylate varies between about 1.2:1 and 3:1.

9. The contact lens of claim 8 where the ratio is about 1.5 to 1.

10. The contact lens of claim 8 where the copolymer is formed in the presence of 0.02 weight percent of a catalyst based upon the weight of the 2,3—dihydroxypropyl methacrylate.

11. The contact lens of claim 7 where the copolymer is formed under conditions whereby a hydrated round button formed from said copolymer having a thickness of 3 mm and a diameter of 12 mm will appear slightly milky when viewed through its cross-section.

12. The contact lens of claim 1 saturated with a drug.

13. The contact lens of claim 1 saturated with water.

14. The contact lens of claim 1 being saturated with an aqueous liquid containing a physiologically active solute.

15. The contact lens of claim 1 where said solute is bacteriostatic.

16. The contact lens of claim 1 having anterior or posterior peripheral curvature or multiple peripheral curvatures.

17. The contact lens of claim 7 saturated with a drug.

18. The contact lens of claim 7 hydrated with water.

19. The contact lens of claim 7 saturated with an aqueous liquid containing a physiologically active solute.

20. The contact lens of claim 7 where the solute is bacteriostatic.

21. The contact lens of claim 7 having anterior and/or posterior peripheral curvature or multiple peripheral curvatures.

22. A free radical, bulk polymerization process for preparing a copolymeric structure suitable for use as a contact lens comprising forming a mixture consisting essentially of two acrylates in the substantial absence of water or other diluent, said first acrylate being hydrophilic and conforming to the formula:

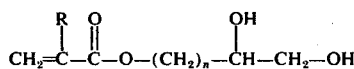

where R is hydrogen or methyl and n is a whole integer having a value of from 0 to 4, and said second acrylate being substantially water insoluble and conforming to the formula:

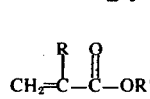

where R is as above described and R' is alkyl having from 1 to 6 carbon atoms, the molar ratio of said first acrylate to said second acrylate varying between 1:1 and 10:1 and causing said mixture to react so as to form a solid, shape-retaining body of copolymer of said two acrylates that is insoluble in a solvent system comprising 60% by volume acetone and 40% by volume dioxane.

23. The process of claim 22 including the step of hydrating the copolymer to form a hydrogel.

24. The process of claim 22 where the mole ratio of said first acrylate to said second acrylate varies between about 1.2:1 and 2:1.

25. The process of claim 22 where R and R' are methyl and n is 1.

26. The process of claim 22 where the reaction temperature is about 40°C.

27. The process of claim 22 where a catalyst is used in an amount of about 0.02% by weight of said first acrylate.

28. The process of claim 27 where the catalyst is isopropylpercarbonate.

29. A contact lens of a copolymer formed by free-radical bulk copolymerization of a mixture consisting essentially of 2,3—dihydroxypropyl methacrylate and methyl methacrylate, the mole ratio of said 2,3—dihydroxypropyl methacrylate to methyl methacrylate varying between 1:1 and 10:1, said copolymer being insoluble in a solvent system comprising 60% by volume acetone and 40% by volume dioxane, said lens being a hydrogel which when hydrated swells linearly between 17 and 19%, absorbs about 39 to 42% liquid and has a durometer hardness of between about 46 to 49.

30. The contact lens of claim 29 having a thickness varying between 0.05mm and 0.15 mm.

31. The contact lens of claim 1, further comprising from about 1% to about 3% by weight, based on said first monomer, of an epoxy compound conforming to the formula:

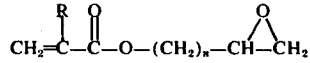

where R is hydrogen or methyl and n is a whole integer having a value of from 0 to 4.

32. The copolymer of claim 31, wherein the epoxy compound is present in an amount of from about 1.8% to about 2.2% by weight based on said first monomer.

* * * * *